US010005866B2

(12) United States Patent
Chen et al.

(10) Patent No.: US 10,005,866 B2
(45) Date of Patent: Jun. 26, 2018

(54) BETAINE-BASED SHAPE MEMORY POLYMER AND PREPARATION METHOD THEREOF

(71) Applicant: SHENZHEN UNIVERSITY, Guangdong (CN)

(72) Inventors: Shaojun Chen, Guangdong (CN); Yangyang Chen, Guangdong (CN); Funian Mo, Guangdong (CN); Yan Yang, Guangdong (CN); Shiguo Chen, Guangdong (CN); Zaochuan Ge, Guangdong (CN)

(73) Assignee: SHENZHEN UNIVERSITY, Shenzhen (CN)

( * ) Notice: Subject to any disclaimer, the term of this patent is extended or adjusted under 35 U.S.C. 154(b) by 187 days.

(21) Appl. No.: 15/243,953

(22) Filed: Aug. 22, 2016

(65) Prior Publication Data

US 2016/0355624 A1 Dec. 8, 2016

Related U.S. Application Data

(63) Continuation of application No. PCT/CN2014/091019, filed on Nov. 13, 2014.

(30) Foreign Application Priority Data

Jul. 24, 2014 (CN) .......................... 2014 1 0357273

(51) Int. Cl.
C08F 220/06 (2006.01)
A61B 17/00 (2006.01)

(52) U.S. Cl.
CPC .. *C08F 220/06* (2013.01); *A61B 2017/00871* (2013.01); *A61L 2400/16* (2013.01)

(58) Field of Classification Search
None
See application file for complete search history.

(56) References Cited

U.S. PATENT DOCUMENTS

2016/0185663 A1* 6/2016 Chen ..................... C08F 220/38
526/229

FOREIGN PATENT DOCUMENTS

CN 1894313 A 1/2007
CN 103923275 A 7/2014

OTHER PUBLICATIONS

1st Office Action of counterpart Chinese Patent Application No. 201410357273.1 dated Dec. 2, 2015.

* cited by examiner

*Primary Examiner* — Catherine S Branch

(57) ABSTRACT

The present disclosure relates to the field of shape memory materials, it discloses a betaine-based shape memory polymer and the preparation method thereof. The polymer is formed through free radical polymerization of an unsaturated betaine monomer, an acrylic monomer, and an ethylene glycol divinyl ether monomer with the addition of an initiator. The betaine-based shape memory polymer has thermosensitive shape memory property and wet sensitive shape memory property, and it has good biocompatibility and an excellent shape memory property, antibacterial property. It is of great potential for use in engineering, construction, daily life and medical service.

9 Claims, 4 Drawing Sheets

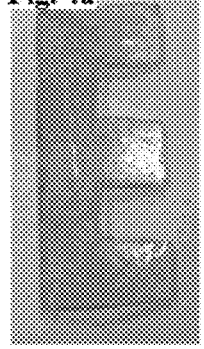 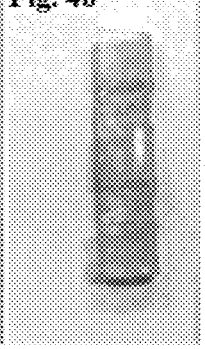 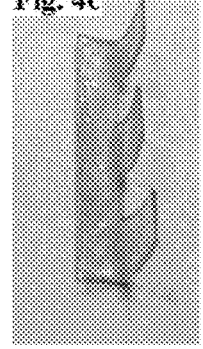 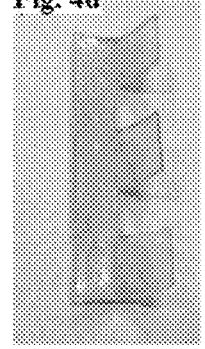 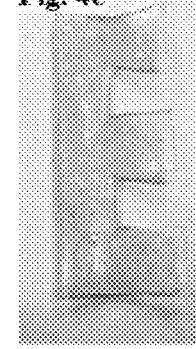
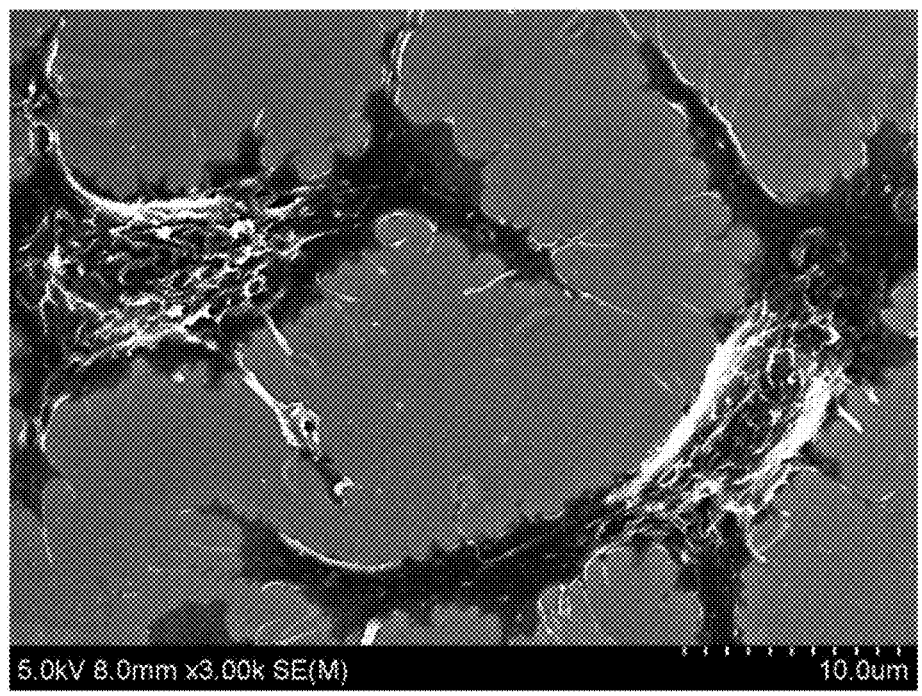
Fig. 5

BETAINE-BASED SHAPE MEMORY POLYMER AND PREPARATION METHOD THEREOF

CROSS-REFERENCE TO RELATED APPLICATIONS

This present application is a Continuation Application of PCT application No. PCT/CN2014/091019 filed on Nov. 13, 2014, which claims the benefit of Chinese Patent Application No. 201410357273.1 filed on Jul. 24, 2014, the contents of which are hereby incorporated by reference.

TECHNICAL FIELD

The present invention relates to the field of shape memory materials, and particularly to a betaine-based shape memory polymer and a preparation method thereof.

BACKGROUND

Shape memory material refers to a material that can sense the environmental change (e.g. temperature, force, electromagnetic, solvent, and other stimulus), and adjust its state parameters (e.g. shape, position, and strain) in response to such a change, so as to recover back to its preset state. Depending on different stimulus conditions, the shape memory material may be, for example, thermosensitive, photosensitive, electrosensitive, or chemically induced. At present, a variety of thermally sensitive shape memory polymers are developed through chemical and physical processes and come into use by researchers at home and abroad. However, the overall performance is generally less desirable. For the purpose of meeting the requirements for use in clinic in biomedicine, the thermally sensitive shape memory polymer needs to have a mild stimulus condition close to the body temperature or adaptable to the bioenvironment, a moderate biological compatibility, a suitable strength, and other properties. Therefore, it is a development tendency in current theoretical and application studies to develop a thermally sensitive shape memory polymer with low cost, excellent comprehensive properties, simple processing process, and good biocompatibility.

The betaine-type zwitterionic polymers refer to a class of polymers that have a structure similar to that of the naturally occurring betaine, and have both a cation and an anion in the same monomer structure. The commonly used sulfobetaine-type amphoteric monomers mainly include vinylpyridine derivatives, acrylamide derivatives, and (meth)acrylate derivatives. Amphoteric polymers with zero net charge and antipolyelectrolyte behavior may be obtained through homopolymerization or copolymerization of these monomers with other neutral monomers under certain conditions. The zwitterionic polymers receive great interest due to the good thermal stability, strong hydration ability, and presence of equal number of quaternary ammonium cation and sulfonate anion that are insusceptible to the pH value of the solution. The hydroxysulfobetaine has not only all the advantages of the zwitterionic compounds, but also resistance to high content of acids, bases, and salts, and good emulsifiability, dispersibility and anti-static performance, as well as microbicidal and anti-mildew effects, viscoelasticity, and others.

The use of shape memory polymers in biomedicine is always a focus of research, and the researchers in the medical and material science communities endeavor to make the medical polymer materials smart, and put them into use in the art of biomedicine. However, most of the shape memory polymers under research is required to be further improved in terms of the biocompatibility. It is found through clinical research that polyurethane shape memory polymer can cause the inflammatory response in human after long-term implantation. Therefore, there is an urgent need for developing a shape memory polymer having a good biocompatibility and superior comprehensive properties, to meet the requirement for use in clinic in biomedicine.

SUMMARY

In light of the technical problems above, the present invention provides a betaine-type polymer having a shape memory property and a good biocompatibility.

The following technical solutions are employed in the present invention. A betaine-based shape memory polymer is provided, which is formed through polymerization of 1 to 50 parts by weight of a monomer A, 1 to 50 parts by weight of a monomer B, and 1 to 20 parts by weight of a monomer C.

The monomer A has the following general formula:

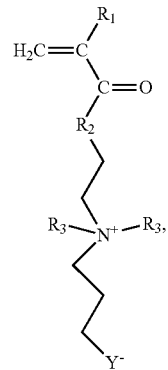

wherein $R_1$ is H or $CH_3$, $R_2$ is O or NH, $R_3$ is any one of $CH_3$, $CH_2CH_3$, and $CH_2CH_2CH_3$, and Y is any one of $COO$, $SO_3$, and $PO_3$.

The monomer B has a general formula of:

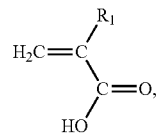

wherein $R_1$ is H or $CH_3$.

The monomer C has a general formula of:

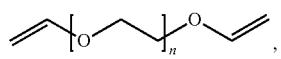

wherein n=1 to 5.

The present invention further provides the method for preparing the shape memory polymer, which comprises the steps of: placing 1 to 50 parts by weight of a monomer A and 1 to 50 parts by weight of a monomer B in a reactor, adding water, and stiffing them until uniform; adding 1 to 20 parts by weight of a monomer C to the reactor, adding additional water and stifling them until uniform; and adding an initiator and reacting at the same temperature to obtain the shape memory polymer.

The monomer A has a general formula of:

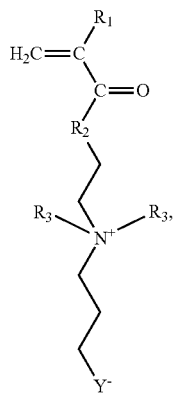

wherein $R_1$ is H or $CH_3$, $R_2$ is O or NH, $R_3$ is one selected from the group consisting of $CH_3$, $CH_2CH_3$, and $CH_2CH_2CH_3$, and Y is one selected from the group consisting of COO, $SO_3$, and $PO_3$.

The monomer B has a general formula of

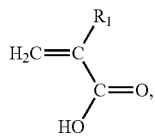

wherein $R_1$ is H or $CH_3$.

The monomer C has a general formula of

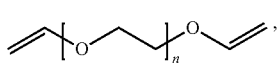

wherein n=1 to 5.

Compared with the prior art, the present invention has the following beneficial effects. A copolymer is prepared through free radical polymerization, in which an unsaturated betaine monomer A is introduced, to allow the polymer to have a good biocompatibility and anti-bacterial property resulted from the betaine polymer; an acrylic monomer B is introduced, to allow the polymer to have a molecular chain with a hydrogen bond structure controlling or affecting the shape memory property of the shape memory polymer; and further an ethylene glycol divinyl ether monomer C is introduced, to allow the polymer to have a cross-linked network structure, thereby increasing the shape memory property and stabilizing the structure of the polymer. The shape memory polymer prepared in the present invention has a good biocompatibility and an excellent shape memory property, thus finding a greatly increased use in biomedicine, medical care, textile industry and other areas. The shape memory polymer may be further used in anti-fouling coating, surface modification of biomaterials, polymerizable permanent antistatic agents, salt resistant polymers and so on, and is of great potential for use in engineering, construction, daily life and medical service.

BRIEF DESCRIPTION OF THE DRAWINGS

FIG. 4a to FIG. 4e are schematic views showing a shape recovery process of a sample of the DMAPS-AA polymer prepared in Example 3.

FIG. 5 is a scanning electron microscope (SEM) photograph of a DMHAS-AA polymer prepared in Example 4 after incubation with macrophages.

DETAILED DESCRIPTION OF THE INVENTION

Figure 1:
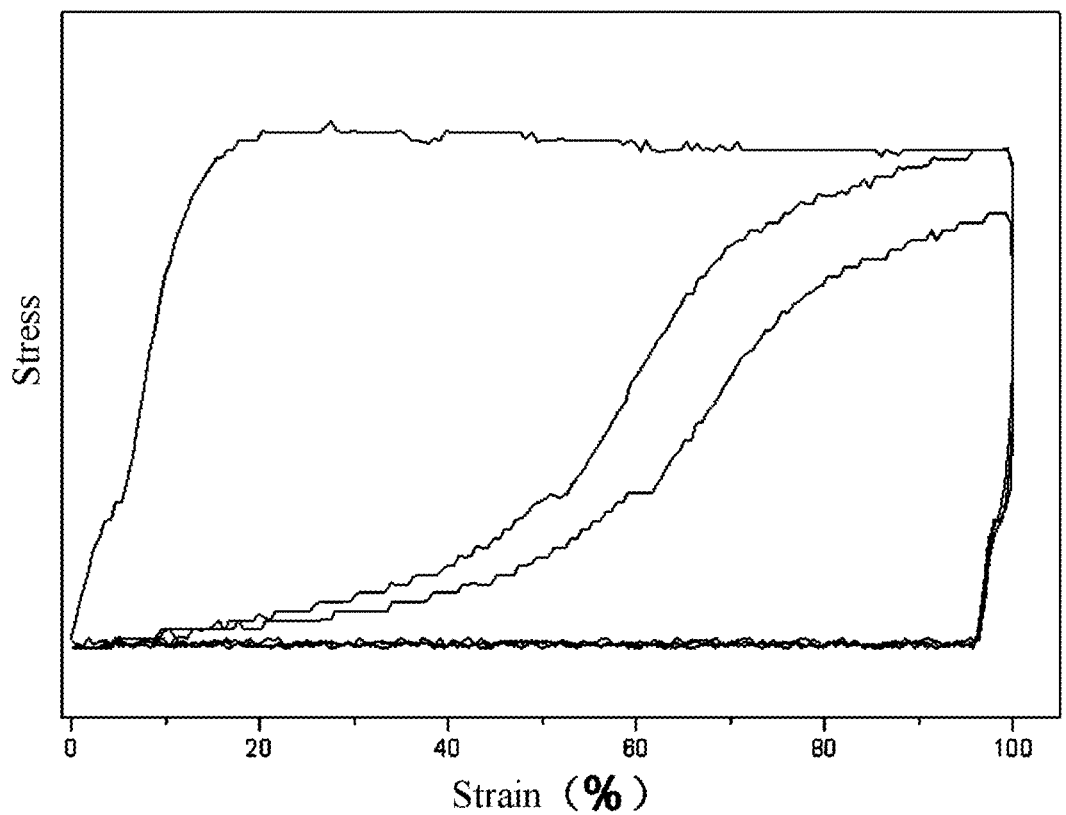
FIG. 1 is a cyclic tensile curve of a DMAPS-AA polymer prepared in Example 1.

To make the technical problem to be solved, the technical solution, and the beneficial effects of the present invention clearer, the present invention is described in further detail with reference to examples. It should be understood that the specific examples described herein are merely provided for illustrating, instead of limiting the present invention.

An example of the present invention provides a betaine-based shape memory polymer, which is formed through polymerization of 1 to 50 parts by weight of a monomer A, 1 to 50 parts by weight of a monomer B, and 1 to 20 parts by weight of a monomer C.

The monomer A has a general formula of

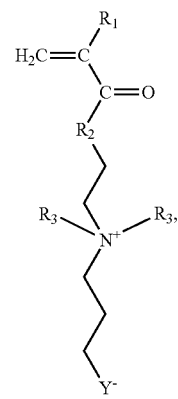

wherein $R_1$ is H or $CH_3$, $R_2$ is O or NH, $R_3$ is one selected from the group consisting of $CH_3$, $CH_2CH_3$, and $CH_2CH_2CH_3$, and Y is one selected from the group consisting of COO, $SO_3$, and $PO_3$.

The monomer B has a general formula of

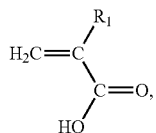

wherein $R_1$ is H or $CH_3$.

The monomer C has a general formula of

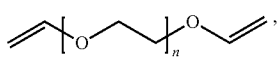

wherein n=1 to 5.

A method for preparing the betaine-based shape memory polymer is further provided, which comprises the steps of:

(1) placing 1 to 50 parts by weight of a monomer A and 1 to 50 parts by weight of a monomer B in a reactor, adding water, and stiffing them until uniform;

(2) adding 1 to 20 parts by weight of a monomer C to the reactor, adding additional water and stiffing them until uniform; and (3) adding an initiator and reacting under the same temperature to obtain the shape memory polymer.

The monomer A has a general formula of

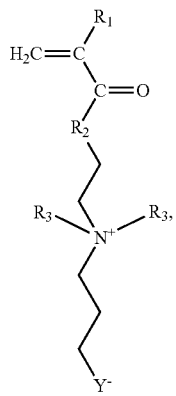

in which $R_1$ is H or $CH_3$, $R_2$ is O or NH, $R_3$ is one selected from the group consisting of $CH_3$, $CH_2CH_3$, and $CH_2CH_2CH_3$, and Y is one selected from the group consisting of COO, $SO_3$, and $PO_3$.

The monomer B has a general formula of

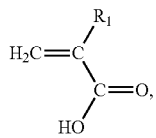

wherein $R_1$ is H or $CH_3$.

The monomer C has a general formula of

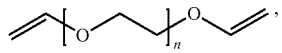

which n=1 to 5.

The initiator used in the reaction is a water-soluble free radical initiator, which may be, for example, ammonium persulfate, potassium persulfate, or a redox initiator. The initiator is firstly formulated into a 1 wt % aqueous solution and then added to the reactor, both of which take place under a protective inert gas atmosphere. The initiator is used in an amount of 0.5 to 2.0% based on the total weight of the monomer A, the monomer B and the monomer C. In the step (2), the three monomers are stirred until uniform, and then heated to about 65° C. in a water bath. The formulated aqueous initiator solution is dropped into the reactor portionwise by means of a dropping funnel. The reaction is continued for 4 to 6 hrs under the same temperature. After the reaction is completed, the reaction solution is cooled to room temperature, and then collected. The water added during the preparation process is deionized water, and the amount is controlled such that the content of the shape memory polymer is 20 to 30 wt %.

In the present invention, a copolymer is prepared through free radical polymerization, in which an unsaturated betaine monomer A is introduced, to allow the polymer to have a good biocompatibility and anti-bacterial property resulted from the betaine polymer; an acrylic monomer B is introduced, to allow the polymer to have a molecular chain with a hydrogen bond structure controlling or affecting the shape memory property of the shape memory polymer; and further an ethylene glycol divinyl ether monomer C is introduced, to allow the polymer to have a cross-linked network structure, thereby increasing the shape memory property and stabilizing the structure of the polymer.

The present invention is further explained by way of specific examples.

EXAMPLE 1

30 g of N,N-dimethyl(methacryloxyethyl)ammonium propanesulfonate (DMAPS) and 50 g of acrylic acid (AA) were added to a reactor, and then deionized water was added and stirred until uniform. Then, 20 g of triethylene glycol divinyl ether was added to the reactor, and further stirred until uniform. Subsequently, deionized water was added to give a final content of the three monomers of 20% by weight in total. Under a nitrogen atmosphere, 1 g of ammonium persulfate was dissolved in 100 mL of deionized water, to provide a 1 wt % aqueous initiator solution. The reactor was heated to 65° C. in a water bath, upon which the aqueous initiator solution was dropped into the reactor portionwise by means of dropping funnel. The reaction was continued at this temperature for 4 hrs. After the reaction was complete, the reaction solution was cooled to room temperature and collected, to afford a DMAPS-AA based shape memory polymer.

Test of shape memory property: The shape memory property of the prepared
DMAPS-AA based polymer was tested. The test result is shown in FIG. 1. It is found through calculation from the data in FIG. 1 that the polymer has a shape fixation rate of about 96%, and a shape recovery rate of about 92%, thus having a good shape memory property.

Figure 2:
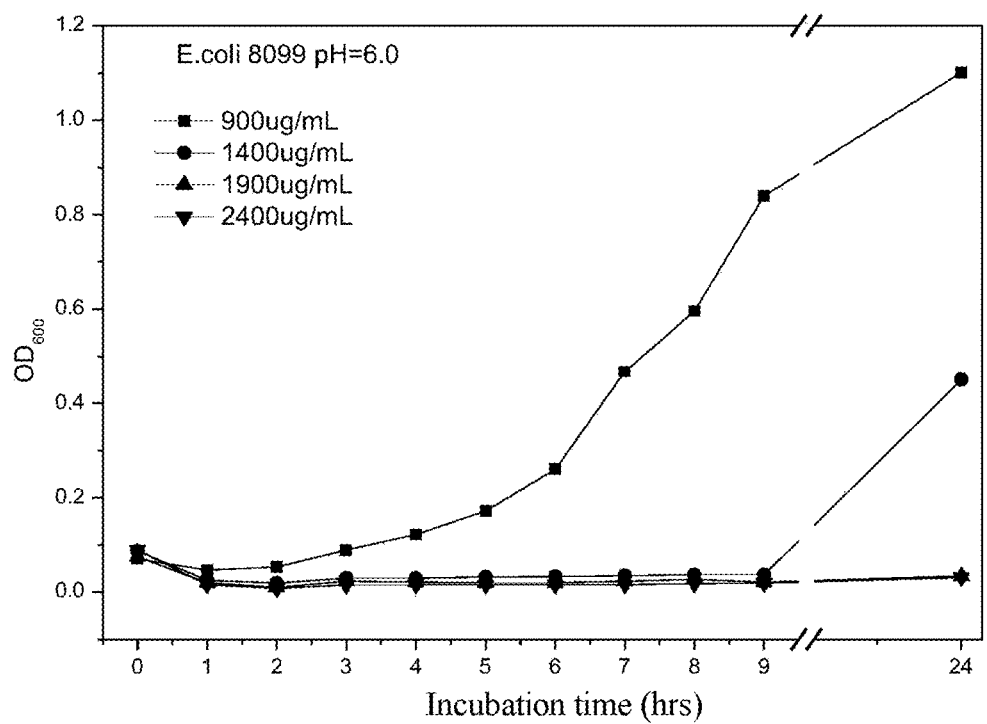
FIG. 2 is a graph of antibacterial test of the DMAPS-AA polymer prepared in Example 1.

Antibacterial test: The antibacterial effect of the prepared DMAPS-AA based polymer was tested with resistance to *E. coli* 8099 as an example. The test result is shown in FIG. 2. It can be seen from FIG. 2 that in the case of a 900 μg/mL polymer solution sample, the $OD_{600}$ value representing the bacterial concentration rises gradually with the elapse of incubation time, indicating increasing number of bacteria. However, the rise in the bacterial number in the solution is unobvious within 4 hrs of incubation, suggesting that the DMAPS-AA based polymer has an inhibition on cell bacterial reproduction. It can be further seen from FIG. 2 that when the concentration of the antibacterial polymer solution is higher than 1900 μg/mL, the $OD_{600}$ value does not rise within 24 hrs, and is persistently 0, that is, no bacteria exist. The result shows that the bacterial reproduction can be effectively inhibited by the DMAPS-AA based polymer when having a content of more than 1900 μg/mL.

EXAMPLE 2

20 g of N,N-dimethyl(methacryloxyethyl)ammonium propanesulfonate (DMAPS) and 50 g of acrylic acid (AA) were added to a reactor, and then deionized water was added and stirred until uniform. Then, 10 g of diethylene glycol divinyl ether was added to the reactor, and further stirred until uniform. Subsequently, deionized water was added to give a final content of the three monomers of 23% by weight in total. Under a nitrogen atmosphere, 1 g of ammonium persulfate was dissolved in 100 mL of deionized water, to provide a 1 wt % aqueous initiator solution. The reactor was heated to 65° C. in a water bath, upon which the aqueous initiator solution was dropped into the reactor portionwise by means of dropping funnel. The reaction was continued at this temperature for 4 hrs. After the reaction was complete, the reaction solution was cooled to room temperature and collected, to afford a DMAPS-AA based shape memory polymer.

Figure 3:
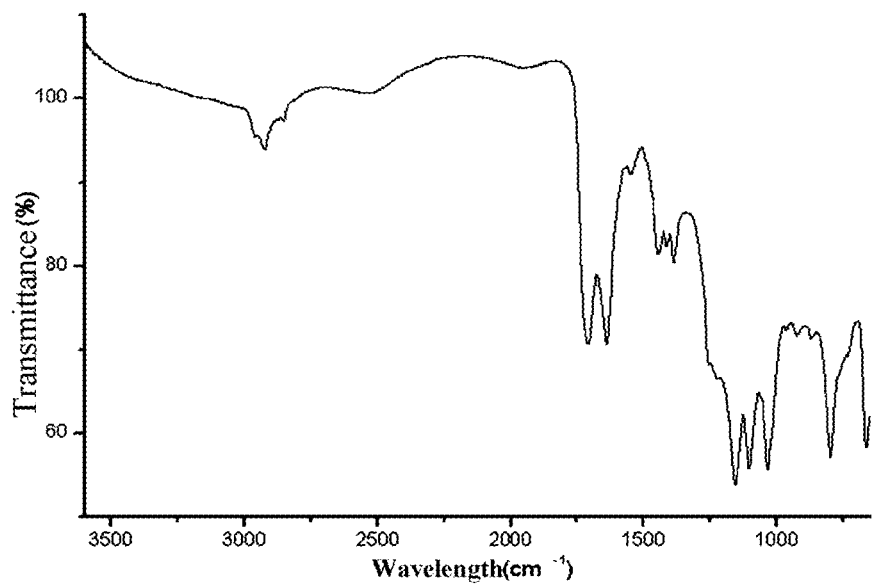
FIG. 3 is an IR spectrum of a DMAPS-AA polymer prepared in Example 2.

The IR spectrum of the prepared DMAPS-AA based polymer is as shown in FIG. 3. In the figure, an IR absorption peak representing the sulfonate structure ($SO_3^-$) appears at 1036 cm$^{-1}$, and an IR absorption peak representing the quaternary ammonium structure (>N$^+$) appears at 960 cm$^{-1}$, suggesting that the prepared polymer is a zwitterionic polymer containing sulfonate and quaternary ammonium.

EXAMPLE 3

15 g of N,N-dimethyl(methacryloxyethyl)ammonium propanesulfonate (DMAPS) and 50 g of methacrylic acid (MA) were added to a reactor, and then deionized water was added and stirred until uniform. Then, 5 g of ethylene glycol divinyl ether was added to the reactor, and further stirred until uniform. Subsequently, deionized water was added to give a final content of the three monomers of 25% by weight in total. Under a nitrogen atmosphere, 1 g of ammonium persulfate was dissolved in 100 mL of deionized water, to provide a 1 wt % aqueous initiator solution. The reactor was heated to 65° C. in a water bath, upon which the aqueous initiator solution was dropped into the reactor portionwise by means of dropping funnel. The reaction was continued at this temperature for 4 hrs. After the reaction was complete, the reaction solution was cooled to room temperature and collected, to afford a DMAPS-MA based shape memory polymer.

The actual shape recovery property of the polymer was tested. FIG. 4a to FIG. 4e are schematic views showing a shape recovery process of a sample. FIG. 4a shows an initial state of the shape memory material; FIG. 4b shows a temporary state of the polymer with fixed deformation; FIG. 4c shows a state of the polymer undergoing shape recovery at 50° C.; FIG. 4d shows a state of the polymer undergoing shape recovery at 70° C.; and FIG. 4e shows a state of the polymer undergoing shape recovery at 80° C. It can be seen from FIGS. 4a to 4e that the prepared polymer can effectively recover back to its initial state at 80° C., and thus has a good shape recovery property. Furthermore, it is also found in the experiment that when a sample with fixed deformation is placed in an aqueous solution at 37° C., the temporary shape of the polymer can be recovered back to its initial state quickly in 10 min, suggesting that the polymer has a good shape recovery property in the body fluid at a normal body temperature of human.

EXAMPLE 4

30 g of N, N-dimethyl-N-methacylamidopropyl-N-propanesulfonate (DMHAS) and 50 g of acrylic acid (AA) were added to a reactor, and then deionized water was added and stirred until uniform. Then, 20 g of triethylene glycol divinyl ether was added to the reactor, and further stirred until uniform. Subsequently, deionized water was added to give a final content of the three monomers of 23% by weight in total. Under a nitrogen atmosphere, 1 g of ammonium persulfate was dissolved in 100 mL of deionized water, to provide a 1 wt % aqueous initiator solution. The reactor was heated to 65° C. in a water bath, upon which the aqueous initiator solution was dropped into the reactor portionwise by means of dropping funnel. The reaction was continued at this temperature for 4 hrs. After the reaction was complete, the reaction solution was cooled to room temperature and collected, to afford a DMHAS-AA based shape memory polymer.

A sample of the prepared DMHAS-AA based polymer was co-incubated with mouse peritoneal macrophages (RAW264.7) for 24 hrs, immobilized for 3 hrs in a 2.5% glutaraldehye solution at 4° C., washed with a PBS buffer, and then air dried at room temperature. The sample was plated with gold by ion sputtering, and observed for the macrophage morphology under a scanning electron microscope. The SEM photograph is as shown in FIG. 5. It can be seen that after co-incubation with the polymer, the macrophages adhere well, and have more pseudopodia and a high phagocytic activity. The polymer prepared according to the present method has a good biocompatibility, and can be effectively and safely used in the art of biomedicine without affecting the normal cell activity.

EXAMPLE 5

30 g of 2-(2-methacryloxyethyldimethylammonium) acetate (DMAC) and 50 g of acrylic acid (AA) were added to a reactor, and then deionized water was added and stirred until uniform. Then, 20 g of triethylene glycol divinyl ether was added to the reactor, and further stirred until uniform. Subsequently, deionized water was added to give a final content of the three monomers of 30% by weight in total. Under a nitrogen atmosphere, 1 g of ammonium persulfate was dissolved in 100 mL of deionized water, to provide a 1 wt % aqueous initiator solution. The reactor was heated to 65° C. in a water bath, upon which the aqueous initiator solution was dropped into the reactor portionwise by means of dropping funnel. The reaction was continued at this temperature for 4 hrs. After the reaction was complete, the reaction solution was cooled to room temperature and collected, to afford a DMAC-AA based shape memory polymer.

Figure 6:
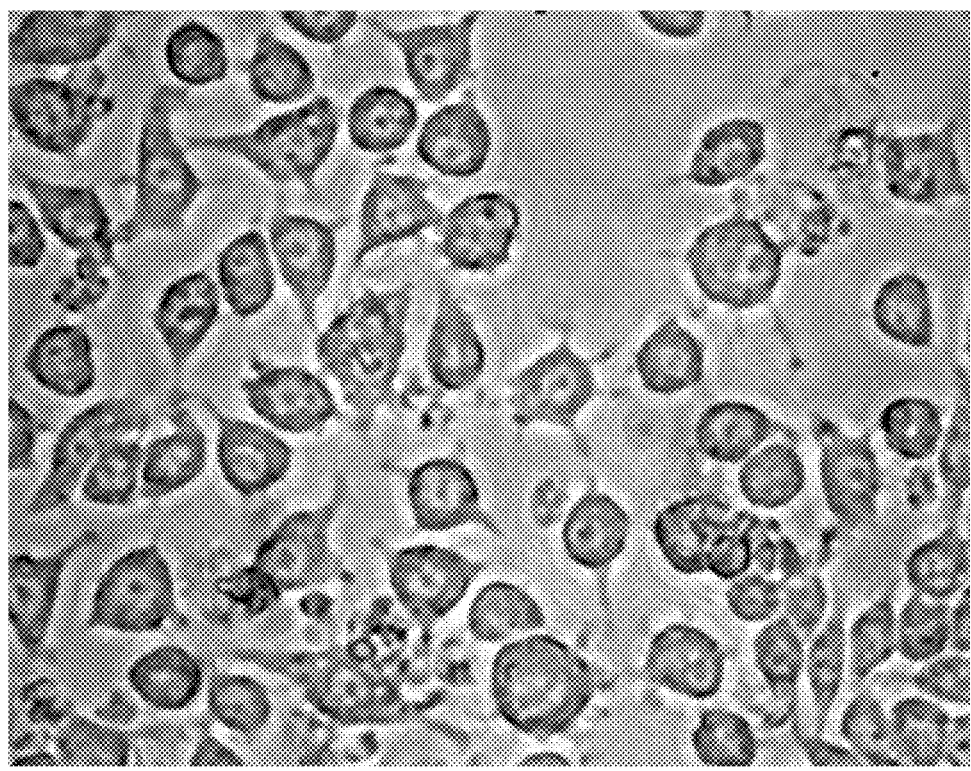
FIG. 6 is an inverted fluorescence microscope (IFM) photograph of the DMAC-AA polymer prepared in Example 5 after incubation with macrophages.

A sample of the prepared DMAC-AA based polymer was co-incubated with mouse peritoneal macrophages (RAW264.7) for 24 hrs, and directly observed for the macrophage morphology under an inverted fluorescence microscope (IFM). As shown in FIG. 6, the morphology of the cells in suspension is sharp in contour, diverse, and oval shaped, suggesting that the mouse macrophages grow normally, and the prepared DMAC-AA based polymer has a good biocompatibility.

In summary, the shape memory polymer prepared in the present invention has a good biocompatibility and an excellent shape memory property, thus finding a greatly increased use in biomedicine, medical care, textile industry and other areas. The shape memory polymer may be further used in anti-fouling coating, surface modification of biomaterials, polymerizable permanent antistatic agents, salt resistant polymers and so on, and is of great potential for use in engineering, construction, daily life and medical service.

The present invention has been described in detail with reference to preferred embodiments, which however are not intended to limit the present invention. Any modifications and equivalent improvements and substitutions can be made thereto without departing from the spirit and principle of the present invention, which are all fall within the protection scope of the present invention.

What is claimed is:

1. A betaine-based shape memory polymer, which is formed through polymerization of 1 to 50 parts by weight of a monomer A, 1 to 50 parts by weight of a monomer B, and 1 to 20 parts by weight of a monomer C;
    wherein the monomer A has a general formula of

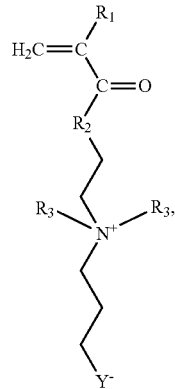

wherein $R_1$ is H or $CH_3$, $R_2$ is O or NH, $R_3$ is one selected from the group consisting of $CH_3$, $CH_2CH_3$, and $CH_2CH_2CH_3$, and Y is one selected from the group consisting of COO, $SO_3$, and $PO_3$;
    the monomer B has a general formula of

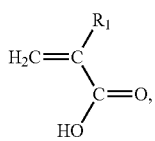

wherein $R_1$ is H or $CH_3$;
    the monomer C has a general formula of

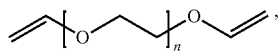

wherein n=1 to 5.

2. A method for preparing a betaine-based shape memory polymer comprising the steps of:
    placing 1 to 50 parts by weight of a monomer A and 1 to 50 parts by weight of a monomer B in a reactor, adding water and stifling until uniform;
    adding 1 to 20 parts by weight of a monomer C to the reactor, further adding water and stirring uniform; and
    adding an initiator to give a mixture and maintaining the mixture at a temperature to obtain the shape memory polymer;
    wherein the monomer A has a general formula of

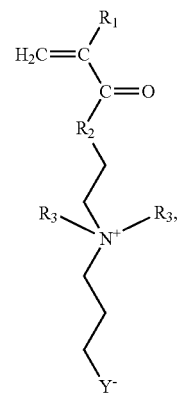

wherein $R_1$ is H or $CH_3$, $R_2$ is O or NH, $R_3$ is one selected from the group consisting of $CH_3$, $CH_2CH_3$, and $CH_2CH_2CH_3$, and Y is one selected from the group consisting of COO, $SO_3$, and $PO_3$;
    the monomer B has a general formula of

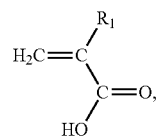

wherein $R_1$ is H or $CH_3$;
    the monomer C has a general formula of

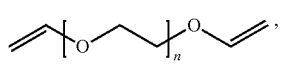

wherein n=1 to 5.

3. The method of claim 2, wherein the initiator is added in an amount of 0.5% to 2.0% based on the total weight of the monomer A, the monomer B and the monomer C.

4. The method of claim 2, wherein the initiator is formulated into 1 wt % aqueous solution prior to being added to the reactor.

5. The method of claim 4, wherein the initiator is formulated and added to the reactor under an inert gas atmosphere.

6. The method of claim 4, wherein the initiator is at least one selected from the group consisting of ammonium persulfate, potassium persulfate, and a redox initiator.

7. The method of claim 2, wherein the temperature is 65° C., and the temperature is maintained for 4 to 6 hrs.

8. The method of claim 2, wherein the water is added in such an amount that the content of the shape memory polymer is 20 wt % to 30 wt %.

9. The method of claim 2, wherein the water is deionized water.

* * * * *